United States Patent [19]
Nagy et al.

[11] Patent Number: 5,650,565
[45] Date of Patent: Jul. 22, 1997

[54] MINI-DILUTION APPARATUS AND METHOD FOR EXHAUST EMISSION TESTING

[75] Inventors: Donald B. Nagy, Canton; Jon Richard McLeod, Hartland; Francis Patrick Schroeder, Fenton; Steven Scott DeCarteret, Royal Oak, all of Mich.

[73] Assignee: Enviromental Sciences Research and Development Partnership, Dearborn, Mich.

[21] Appl. No.: 498,317

[22] Filed: Jul. 5, 1995

[51] Int. Cl.⁶ ................................................. G01M 15/00
[52] U.S. Cl. ........................................ 73/199; 73/195; 73/203
[58] Field of Search ........................... 73/195, 198, 199, 73/200, 203

[56] References Cited

U.S. PATENT DOCUMENTS

| | | | |
|---|---|---|---|
| 3,593,023 | 7/1971 | Dodson et al. | 73/23.32 |
| 3,699,814 | 10/1972 | Kaufman | 73/863.11 |
| 4,361,028 | 11/1982 | Kamiya et al. | 73/23.32 |
| 4,372,155 | 2/1983 | Butler et al. | 73/23.32 |
| 4,586,367 | 5/1986 | Lewis | 73/116 |
| 4,660,408 | 4/1987 | Lewis | 73/28.06 |
| 4,823,591 | 4/1989 | Lewis | 73/3 |
| 5,090,258 | 2/1992 | Yamasaki et al. | 73/863.03 |
| 5,196,170 | 3/1993 | Patashnick et al. | 73/863.23 |
| 5,279,970 | 1/1994 | Patashnick et al. | 73/28.01 |
| 5,401,468 | 3/1995 | Patashnick et al. | 73/863.23 |

OTHER PUBLICATIONS

SAE Technical Paper Series 930141, A Sampling for the Measurement of PreCatalyst Emissions from Vehicles Operating Under Transient Conditions. Jon McLeod et al., Published Mar. 1, 1993.

*Primary Examiner*—Richard Chilcot
*Assistant Examiner*—Eric S. McCall
*Attorney, Agent, or Firm*—Fildes & Outland, P.C.

[57] ABSTRACT

A mini-diluter apparatus and method are provided for preparing dilute samples of exhaust gas for emission testing. The apparatus includes first and second mass flow controllers which respectively control the mixing of exhaust gas and diluent gas samples at a constant ratio. The mixture is fed at a pressure, controlled by a back pressure regulator, to a third mass flow controller. This third controller provides a controlled sample rate (normally proportional to exhaust flow from an engine under test) to a bag sample system, or other sampling system, with excess mixture being exhausted through a pressure regulator to atmosphere. Improved accuracy and reduced calibration complexity are results of the improved apparatus and method.

8 Claims, 3 Drawing Sheets

MINI-DILUTION APPARATUS AND METHOD FOR EXHAUST EMISSION TESTING

FIELD OF THE INVENTION

This invention relates to measurement of automobile engine emissions and in particular to a mini-diluter apparatus and method for preparing dilute samples of exhaust gas for emission testing.

BACKGROUND OF THE INVENTION

SAE Technical Paper 930141 published Mar. 1, 1993, entitled A Sampling System for the Measurement of Pre-Catalyst Emissions from Vehicles Operating Under Transient Conditions provides a full description of such a system. That system incorporates a so called "mini-diluter" utilizing a pair of mass flow controllers externally controlled to provide a mixture of exhaust gas and diluent gas in a prescribed ratio and at a flow rate related to the flow of exhaust through the vehicle. The mixture of diluted exhaust and diluent is provided to a plurality of bag samplers for collection of samples.

FIG. 1 illustrates the mini-diluter portion of this prior art sampling system as described in the SAE paper. It shows the appropriately labeled exhaust gas pipe (exhaust), an exhaust mass flow controller (MFM) actuated by a control circuit and exhaust flow signal, a diluent mass flow controller (MFM) connected with a source of zero air, a sample pump (metal bellows pump) and three sample bags connected with the pump.

While the mini-diluter sampling system discussed has been successfully utilized, it is found necessary to periodically check the calibrations of the two mass flow controllers at a number of points across their complete range of operation and to establish, at least initially, the relative accuracy of the flow rates of the two mass flow controllers over the range of flow conditions. Because the flow rates of the two mass flow controllers at various flow settings are not linear and may have differing response times, the repeated calibration of these devices requires considerable time and the resulting accuracy of the measurements is limited, although adequate for the purposes intended.

SUMMARY OF THE INVENTION

The present invention provides an improved mini-diluter apparatus for preparing dilute samples of exhaust gas for emission testing. The apparatus may be used in a bag testing system as described in the above mentioned SAE Paper 930141, as well as in continuous emission testing systems, and has been found to improve both the ease of calibration of the apparatus and the accuracy of the results obtained therefrom.

In essence, the improved mini-diluter apparatus allows the first pair of mass flow controllers to be operated at a selected constant flow rate to provide a constant flow controlled mixture of exhaust gas and diluent gas for subsequent exhaust sampling operations. The apparatus adds a third mass flow controller in a pressurized transfer line downstream of the mixture ratio controllers. The third mass flow controller is operated to vary the flow of mixture delivered to the emission collection bags or other testing equipment. In accordance with the currently preferred sampling method, the sample collection flow is varied proportionally to the exhaust flow from the engine being sampled. Excess mixture provided is exhausted by a pressure regulator. The apparatus thus simplifies calibration since the first pair of mass flow controllers need to be calibrated only at the constant flow point or points for each controller and the variable flow controller is checked against its single curve for repeatability. Accuracy of the sample repeatability is improved from about 20% error to less than 5% error.

These and other features and advantages of the invention will be more fully understood from the following description of certain exemplary embodiments of the invention taken together with the accompanying drawings.

DETAILED DESCRIPTION OF THE INVENTION

Figure 2:
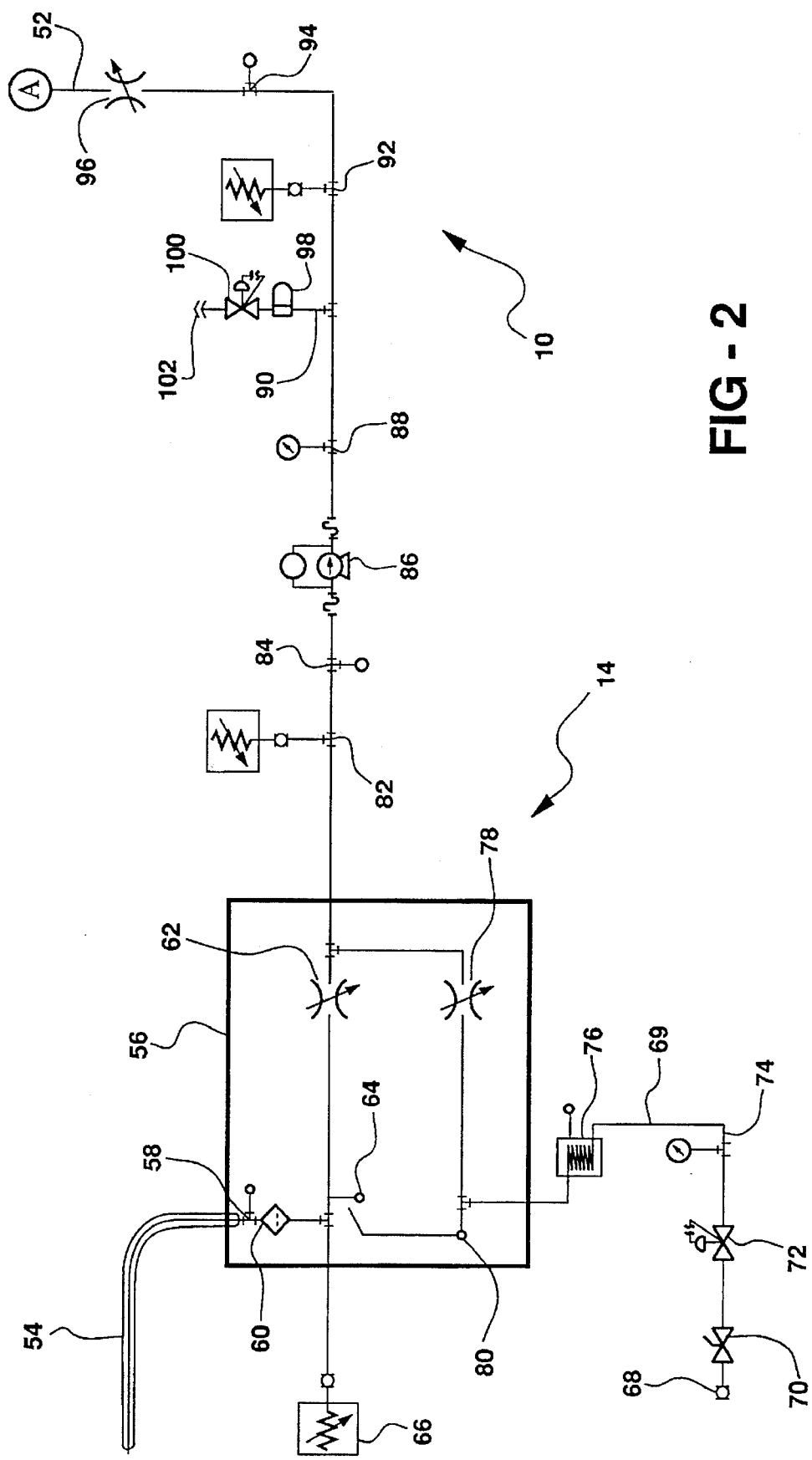
FIGS. 2 and 3 comprise a line diagram of an improved mini-diluter sampling system and apparatus formed according to the invention.
Figure 3:
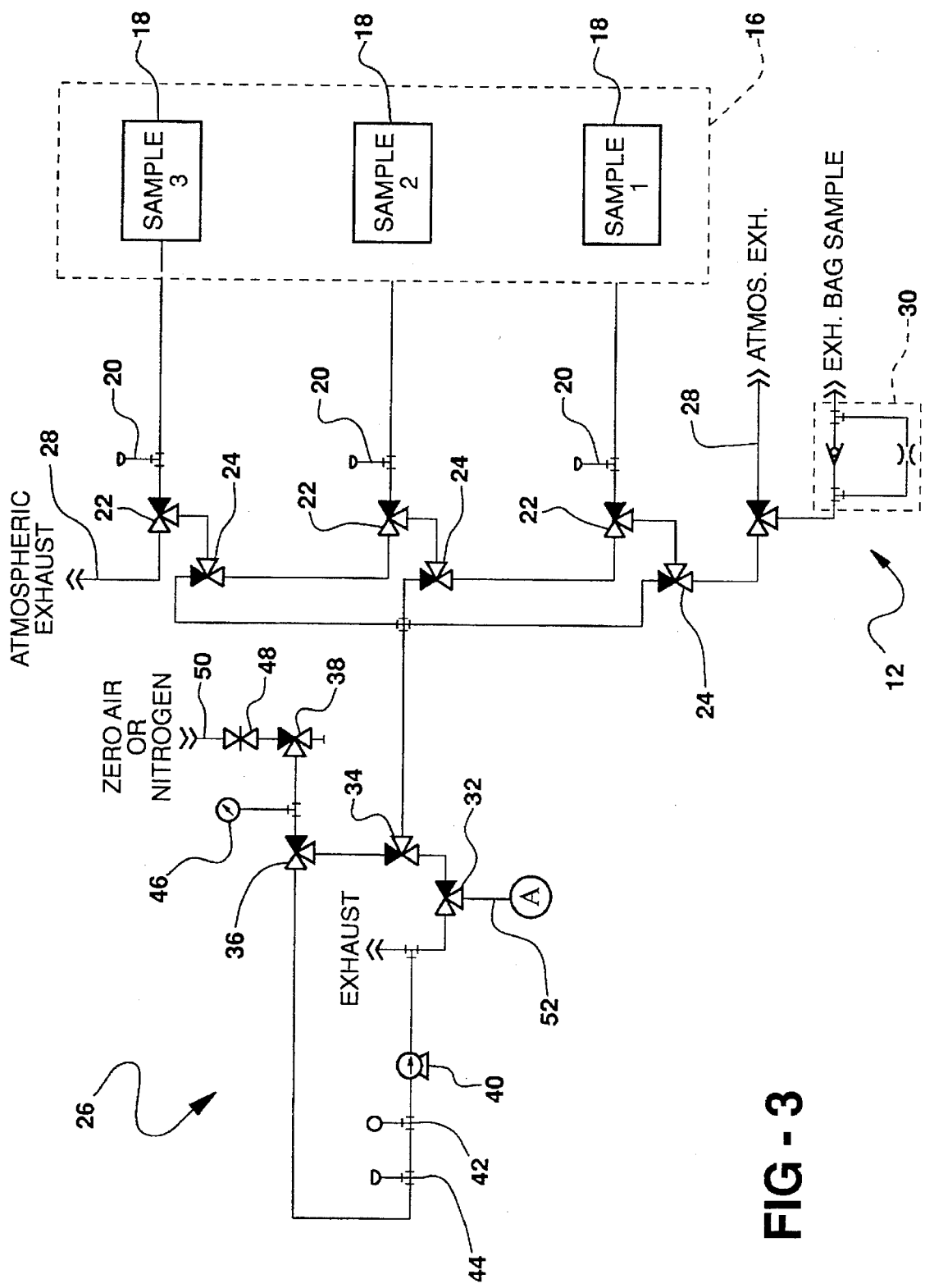

Referring now to FIGS. 2 and 3 of the drawings in detail, numeral 10 generally indicates a bag type sampling system including sample receiving and control apparatus. The sample apparatus 12 (FIG. 3) is a known arrangement and it should be understood that other types of sampling apparatus, such as apparatus for continuous sampling, could equally well be connected with the mini-diluter apparatus 14 (FIG. 2) of the present invention.

Sampling apparatus 12, shown in FIG. 3, includes a suitable support 16 for carrying, for example, three sample bags 18, each of which is removably connected through a vacuum switch 20 and solenoid valves 22 and 24 with supply and purge apparatus 26, as well as with exhaust lines 28 and a separate bag analysis port 30. The supply apparatus 26 includes solenoid valves 32, 34, 36, 38 connecting with an evacuator pump 40 connected with a vacuum gage 42 and vacuum switch 44 and a pressure gage 46 adjacent to a needle valve 48 controlling the feed from a purge source of zero air or nitrogen gas 50. Apparatus 26 connects the sample bags 18 with the mini-diluter apparatus 14 through the connection of valve 32 with a transfer line 52.

The mini-diluter apparatus 14, shown in FIG. 2, includes a heated exhaust gas line 54 extending into a temperature controlled oven 56 where it connects, through a thermocouple 58 and filter 60, with a first mass flow controller 62. A temperature sensor 64 and pressure transducer 66 are also connected with the exhaust gas line 54 for measuring temperature and pressure of the gas fed to the mass flow controller 62. At its other end, exhaust gas line 54 is adapted for connection with a tailpipe or other portion of the exhaust system of a vehicle or engine for obtaining raw exhaust gas samples therefrom.

Also provided is a source 68 of diluent gas, such as nitrogen or zero air (that is free from water and other measurable emission constituents). Source 68 connects via diluent gas line 69 through a toggle valve 70, forward pressure regulator 72, pressure gage 74, and an axial heater 76 with a second mass flow controller 78. Located within the oven 56, a temperature sensor 80 is also provided to indicate the gas temperature being supplied to the second mass flow controller 78.

Mass flow controllers 62, 78 have outlets which are connected together through the transfer line 52 to mix their outgoing gas constituents. The mixed flow samples in the transfer line are directed from the two controllers 62, 78 past a pressure transducer 82 and a temperature sensor 84, through a sample pump 86 and past a pressure gage 88, a bypass line 90, a pressure transducer 92 and a temperature sensor 94 to a third mass flow controller 96 which connects with valve 32 of the supply apparatus 26. The bypass line 90 connects with an accumulator 98 and a back pressure regulator 100 which exhausts excess flow through an exhaust port 102.

Figure 1:
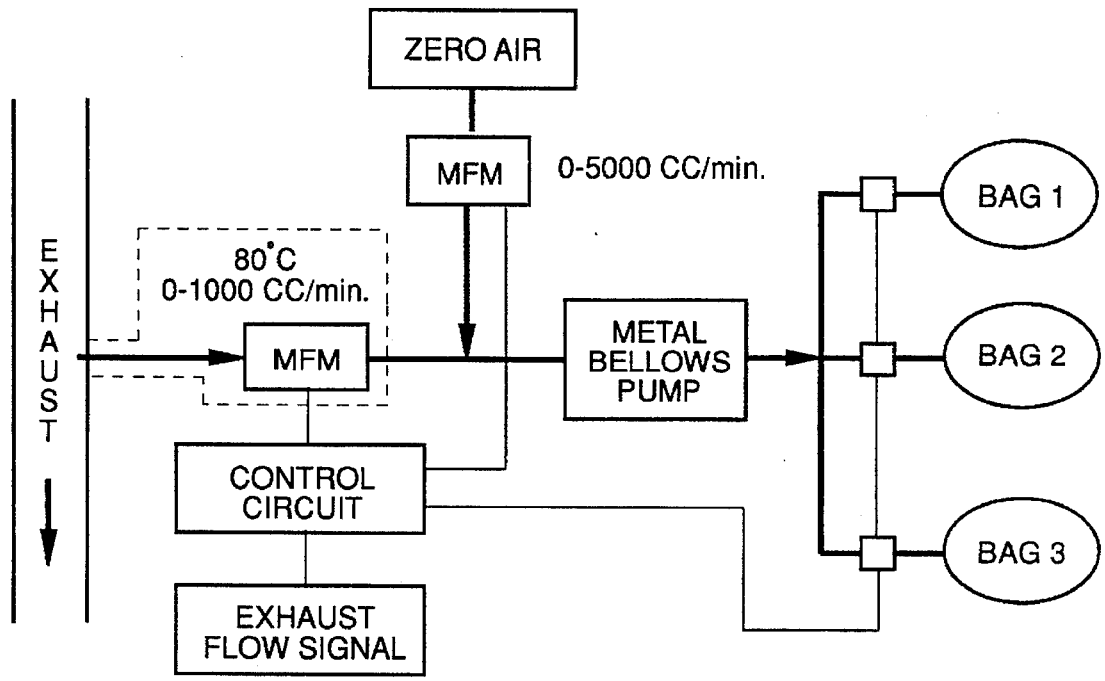
FIG. 1 is a block diagram of a prior art mini-diluter sampling system.
Figure 4:
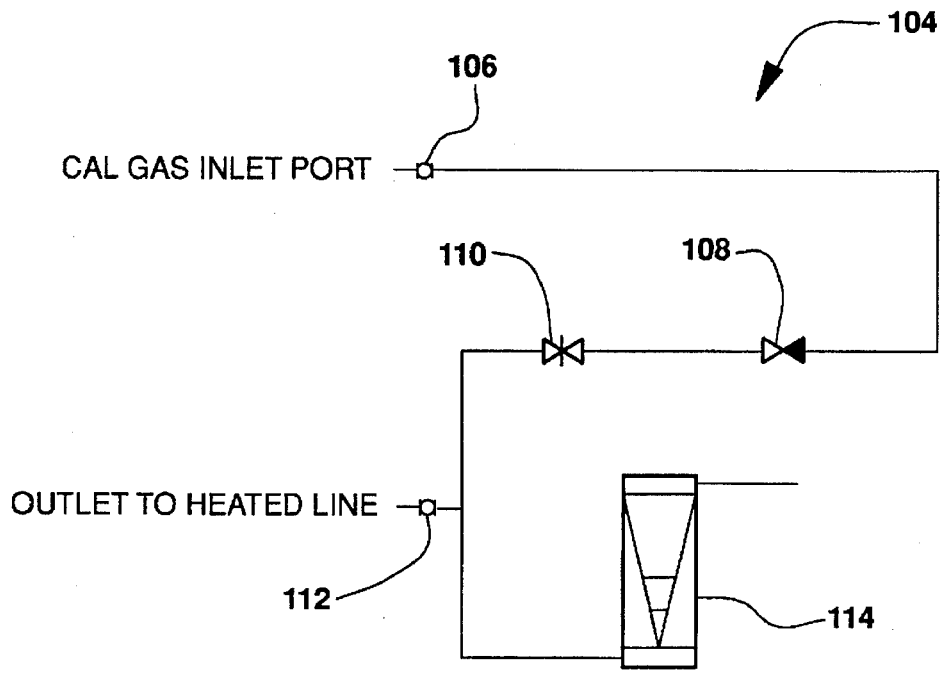
FIG. 4 is a line diagram of an associated calibration apparatus.

FIG. 4 shows an associated calibration apparatus 104 that includes a calibration gas inlet port 106, connected through a solenoid valve 108 and a controlling needle valve 110, with an outlet 112 which is connectable with the exhaust gas heated line 54 for calibration purposes. A rotometer 114 is also provided to indicate calibration gas bypassed during the calibration process.

In operation, the heated line 54 is connected with an engine or vehicle exhaust system and receives exhaust gas samples at a rate controlled by mass flow controller 62. The sample pump 86 is operated to provide at least the minimum pressure drop across this first mass flow controller 62 which is required for accurate flow control. Concurrently, diluent gas line 69 receives a diluting gas such as zero air or nitrogen from source 68. The diluent gas is fed at a pressure controlled by forward pressure regulator 72 through the axial heater 76 where it is heated to the temperature of the oven 56. From heater 76, the gas is passed into the oven and through the second mass flow controller 78 which controls the rate of diluent gas flow through line 69.

The controlled flow rates of exhaust gas and diluent gas through flow controllers 62, 78, determine the ratio of exhaust gas to diluent in the mixture that is formed by joining of the outlets of the two mass flow controllers at their connection to the transfer line 52. This diluted mixture is then drawn into the transfer line 52 by the sample pump 86 which, in effect, sucks the exhaust gas samples from the engine or vehicle exhaust pipe for mixing with the diluent gas from line 69.

The pump 86 delivers the dilute mixture under pressure past the bypass line 90 to the third mass flow controller 96. This controller 96 controls the flow rate of the diluted samples from the mini-diluter into the supply system and the sample bags 18 fed thereby. This flow, as in the sampling system discussed in the previously mentioned SAE paper 930141, is controlled as a function of gas flow through the engine exhaust system being sampled and therefore varies with the engine exhaust flow conditions.

To provide accuracy of the mixture ratio, the flow rates through the first and second mass flow controllers 62 and 78 are maintained constant for each test condition although the rate of constant flow may be varied for differing conditions. Accordingly, excess mixture, beyond that allowed to flow through the third mass flow controller 96, is delivered to the bypass line 90. This excess mixture is exhausted through the back pressure regulator 100 and exhaust port 102. The back pressure regulator, thus controls the pressure at a preselected value between the sample pump 86 and mass flow controller 96 in the pressurized portion of the transfer line 52. This creates a minimum pressure differential across the third mass flow controller 96 to assure its accurate control of the mass flow according to a pre-measured and known flow curve.

The accumulator 98 is provided to damp out pressure pulses in the transfer line 52 which would otherwise be caused by the pumping action of the sample pump 86.

Location of the accumulator in the bypass line 90 prevents mixture exhausted from the accumulator from affecting the composition of dilute mixture samples flowing through the transfer line 52.

Referring to FIG. 4, when calibration of the system is required, calibration gas is received through port 106 into apparatus 104. The calibration gas is admitted through solenoid valve 108 at a rate established by needle valve 110 and delivered through outlet 112 to the gas line 54. The calibration gas is fed through the sampling system 10 as if it were engine exhaust gas and the known constituents are measured by the sampling system to determine and calibrate the system for accuracy. The rotometer 114 in the calibration system indicates the amount of calibration gas being bypassed from the system and shows that only calibration gas is being fed through the outlet 112.

The improved mini-diluter apparatus 14 provides accurate and easily controllable mixture samples to the sample bags 18. This results from the fact that the first and second mass flow controllers 62, 78 are operated at selected constant flow rates to provide a predetermined mixture ratio of exhaust gas sample to diluent gas, and this mixture is then fed through the third mass flow controller which is able to accurately deliver varying flow rates of mixture to the sample bags. The sample flow rates are preferably controlled by the third mass flow controller 96 to be proportional to exhaust flow of the vehicle under test. The use of the three mass flow controllers in this manner, accompanied by temperature and pressure controlling devices for maintaining accuracy of flow and delivery, provides an improved mini-diluter apparatus requiring a minimum of calibration complexity and providing significantly improved accuracy and repeatability of gas samples over the prior mini-diluter system.

While the invention has been described by reference to various specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. Mini-diluter apparatus for preparing dilute samples of exhaust gas for emission testing, said apparatus including:

a first mass flow controller connected in an engine exhaust sample line;

a second mass flow controller connected in a diluent gas line;

said controllers each having an outlet connected with a transfer line to provide a dilute exhaust mixture having a selected ratio of exhaust gas to diluent established by a ratio of flow settings of said first and second controllers;

a pump in said transfer line to maintain a minimum pressure drop through the first controller and pressurize the transfer line downstream of the pump;

said apparatus characterized by:

a third mass flow controller in said transfer line downstream of the pump and connectable with at least one sample receiver, said third controller being operable to transmit a controlled flow of said dilute mixture for delivery to the receiver; and pressure relief apparatus connected with said pressurized transfer line between said pump and said third controller to exhaust excess dilute mixture from said transfer line;

whereby said first and second controllers provide a selected dilute exhaust mixture to the transfer line and said third controller controls the amount of the dilute mixture delivered to the receiver.

2. The invention as in claim 1 characterized by temperature controllers for controlling the temperatures of exhaust samples and diluent gas fed to said first and second mass flow controllers.

3. The invention as in claim 2 characterized by temperature and pressure indicators connected in the transfer line for indicating the fluid conditions.

4. The invention as in claim 1 characterized by a pressure controller for maintaining a minimum pressure drop across said second mass flow controller.

5. The invention as in claim 4 characterized in that said pressure controller is a pressure regulator in said diluent gas line.

6. The invention as in claim 1 characterized in that said pressure relief apparatus is a pressure regulator that exhausts excess flow from said transfer line to maintain a selected pressure input to said third mass flow controller.

7. The invention as in claim 6 characterized in that said pressure regulator is located in a bypass line connected with the transfer line and an accumulator is disposed in the bypass line between the pressure regulator and the transfer line for damping pressure pulses transmitted by the pump without distorting the composition of mixture flow passing through the transfer line.

8. Mini-diluter apparatus for preparing dilute samples of exhaust gas for emission testing, said apparatus including:

a first mass flow controller connected in an engine exhaust sample line maintained at a controlled temperature, the first controller maintained at above a minimum pressure drop;

a second mass flow controller connected in a diluent gas line maintained at a controlled temperature and inlet pressure to the second controller;

said controllers each having an outlet connected with one another and with a transfer line to provide a dilute exhaust mixture having a ratio of exhaust gas to diluent established by a ratio of flow settings of said first and second controllers;

a sample pump in said transfer line and drawing gas through said first controller, said pump pressurizing the transfer line downstream thereof;

said apparatus characterized by:

a third mass flow controller in said pressurized transfer line and connectable with at least one sample receiver, said third controller being operable to transmit a selected variable flow of dilute mixture for delivery to the receiver; and a back pressure regulator connected with said pressurized transfer line and exhausting excess dilute mixture to maintain a controlled pressure in the transfer line;

whereby said first and second controllers operate above a minimum pressure drop and provide a constant mass flow of dilute exhaust mixture to the transfer line and said third controller allows passage of only a controlled flow of dilute mixture for delivery to the receiver with excess flow being exhausted by the back pressure regulator.

\* \* \* \* \*